US008128285B2

(12) United States Patent
Burton

(10) Patent No.: US 8,128,285 B2
(45) Date of Patent: Mar. 6, 2012

(54) X-RAY POSITION FIXTURE AND CASSETTE HOLDER FOR CHILDREN

(76) Inventor: Leslie Burton, Olathe, KS (US)

( * ) Notice: Subject to any disclaimer, the term of this patent is extended or adjusted under 35 U.S.C. 154(b) by 161 days.

(21) Appl. No.: 12/590,540

(22) Filed: Nov. 10, 2009

(65) Prior Publication Data

US 2010/0158199 A1 Jun. 24, 2010

Related U.S. Application Data

(60) Provisional application No. 61/199,273, filed on Nov. 14, 2008.

(51) Int. Cl.
*G03B 42/02* (2006.01)
*G03B 42/04* (2006.01)

(52) U.S. Cl. ............. 378/178; 378/177; 378/180; 5/601

(58) Field of Classification Search .................. 378/177, 378/178, 179, 180, 209; 5/601
See application file for complete search history.

(56) References Cited

U.S. PATENT DOCUMENTS

| | | | | |
|---|---|---|---|---|
| 2,926,256 | A * | 2/1960 | Rankin | 378/174 |
| D282,872 | S * | 3/1986 | Hayes et al. | D24/161 |
| 4,699,425 | A * | 10/1987 | Ohlson | 297/344.24 |
| 4,831,644 | A * | 5/1989 | Lopez | 378/178 |
| 5,023,899 | A * | 6/1991 | Ohlson | 378/196 |
| 5,157,707 | A * | 10/1992 | Ohlson | 378/181 |
| 5,503,411 | A * | 4/1996 | Sundberg et al. | 280/1.188 |
| 5,600,702 | A * | 2/1997 | Pigg | 378/180 |
| 5,761,539 | A * | 6/1998 | Foley et al. | 396/1 |
| 5,764,724 | A * | 6/1998 | Ohlson | 378/177 |
| 6,515,286 | B2 * | 2/2003 | Kuwabara | 250/370.11 |
| 6,523,731 | B1 * | 2/2003 | Pedrini | 224/537 |
| 6,631,948 | B1 * | 10/2003 | Tsuge | 297/195.12 |
| 6,775,867 | B1 * | 8/2004 | Kuphal et al. | 5/601 |
| 6,835,141 | B2 * | 12/2004 | Eaves | 472/97 |
| 6,868,998 | B2 * | 3/2005 | Dean | 224/324 |
| 7,144,024 | B2 * | 12/2006 | Falkner et al. | 280/202 |
| 7,775,893 | B2 * | 8/2010 | Blumenthal | 472/95 |
| 7,780,500 | B2 * | 8/2010 | Sonner et al. | 446/95 |

* cited by examiner

*Primary Examiner* — Allen C. Ho
(74) *Attorney, Agent, or Firm* — Mark Manley

(57) ABSTRACT

A fixture for use in taking X-ray images of children comprising; a base including cylinder having a height adjustable piston, and at least one mounting arm. The mounting arm including a first end connected to the front wheel of a bike and a second end connected to a rear wheel of the bike. The bike including a first seat; a second seat portion supported by the mounting arm, the second seat including a back portion that is transparent to X-rays. An x-ray cassette is mounted on a swivel arm and can be positioned to take typical x-ray images of a child's torso including anterior, posterior, left lateral and right lateral. The fixture can work with any x-ray source and can work with wall mounted x-ray cassettes as well.

13 Claims, 7 Drawing Sheets

16
306
308
310
402
340
342
348
320
342
340
344
322
330A
302
360
304
308
300
A

A
322
302
304
220
300
306
360
203
202
200
230
234
236

X-RAY POSITION FIXTURE AND CASSETTE HOLDER FOR CHILDREN

CROSS REFERENCES TO RELATED APPLICATIONS

Priority is claimed to provisional patent application 61/199,273 "X-Ray Position Fixture for children" filed Nov. 14, 2008

STATEMENT AS TO RIGHTS TO INVENTIONS MADE UNDER FEDERALLY SPONSORED RESEARCH AND DEVELOPMENT

Not Applicable

BACKGROUND OF THE INVENTION

1. Field of the Invention

This invention relates to a device and method of ergonomically supporting a child for X-ray.

2. Brief Description of Prior Art.

There is a need to take X-rays of patients of all range of ages. The youngest, those from new born to 5 years are difficult to study using x-rays because they do not understand what is being done. They do not understand to stay still and may become frightened by the strange equipment and sterile environment. X-ray technicians struggle to find ways to position these young patients and struggle even more to keep them positioned.

Patents such as U.S. Pat. Nos. 4,464,780 and 5,600,702 are examples of the prior art that attempt to confine a child patient for x-ray. Small children are sometimes frightened when restrained in these devices.

As will be described, the preferred embodiments of the present invention overcome disadvantages of the prior art.

SUMMARY OF THE INVENTION

A fixture for positioning a young patient for X-ray study. A fixture for use in taking X-ray images of children comprising; a base including cylinder having a height adjustable piston, and at least one mounting arm. The mounting arm including a first end connected to the front wheel of a bike and a second end connected to a rear wheel of the bike. The bike including a first seat; a second seat portion supported by the mounting arm, the second seat including a back portion that is transparent to X-rays. An x-ray cassette is mounted on a swivel arm and can be positioned to take typical x-ray images of a child's torso including anterior, posterior, left lateral and right lateral. The fixture can work with any x-ray source and can work with wall mounted x-ray cassettes as well.

The present invention will be illustrated on the basis of the figures and following description of a preferred embodiment thereof.

DESCRIPTION OF THE PREFERRED EMBODIMENT

Figure 1:
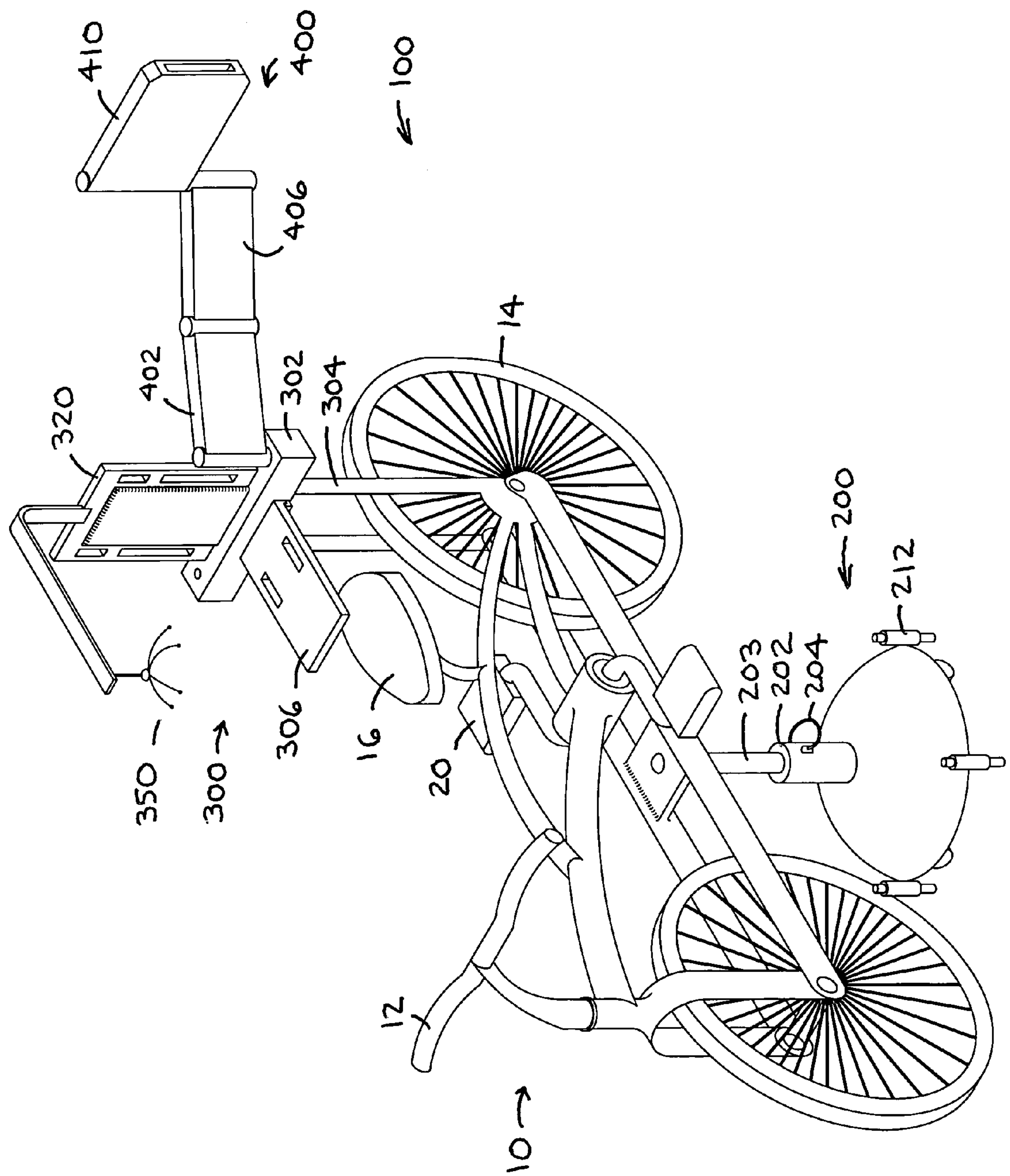
FIG. 1 shows a view of the device ready for use.

In accordance with the present invention, FIG. 1 shows a view of the X-ray fixture 100 designed for use with children. The fixture 100 includes a child's riding toy such as a bike 10. The bike 10 is essentially a standard child's bike that could be purchased in a store. An important aspect of the invention is that most children will immediately recognize the bike 10 and be attracted to it. The fixture 100 also includes an adjustable base 200, a seat portion 300 and an adjustable cassette holder 400.

The bike 10 can include handle bars 12, wheels 14 and a seat portion 16. The bike 10 is a standard child's bike, the only modification being that the pedals 20, handle bar 12 and wheels 14 can be fixed so that they will not rotate to improve safety and reduce distractions.

The base 200 as height adjustable enabling the fixture to be raised and lowered to aid in alignment with existing X-ray equipment. The base 200 includes a piston 203 and cylinder 202 and a foot control 204 to raise and lower the bike 10. The base 200 also includes castor wheels 230 that allow the fixture 100 to be rolled around for transport and positioning and foot operated locks 212 that can lock the base 200 in place for use. The base 200 includes 2 mounting arms 220 that can be used to bolt to the bike 10 at the wheel 14 axles. The mounting arms 220 are attached to the piston 203 of the cylinder 202.

The seat 300 includes a mounting block 302 supported from two support arms 304 attached to the mounting arms 220 adjacent the wheels 14. The mounting block supports a removable transparent acrylic seat bottom 306 and an acrylic seat back 320 that is also transparent to X-ray. There can be a second toy such as a mobile 350 mounted to the fixture 100 such as to the seat back 320 as shown.

An adjustable cassette holder 400 can be rotatably mounted on either end of the mounting block 302. The holder 400 can include a first rotatable arm section 402 and a second rotatable arm section 406 and a cassette mounting tray 410 into which a cassette containing X-ray film or a digital x-ray transducer can be mounted.

Figure 2:
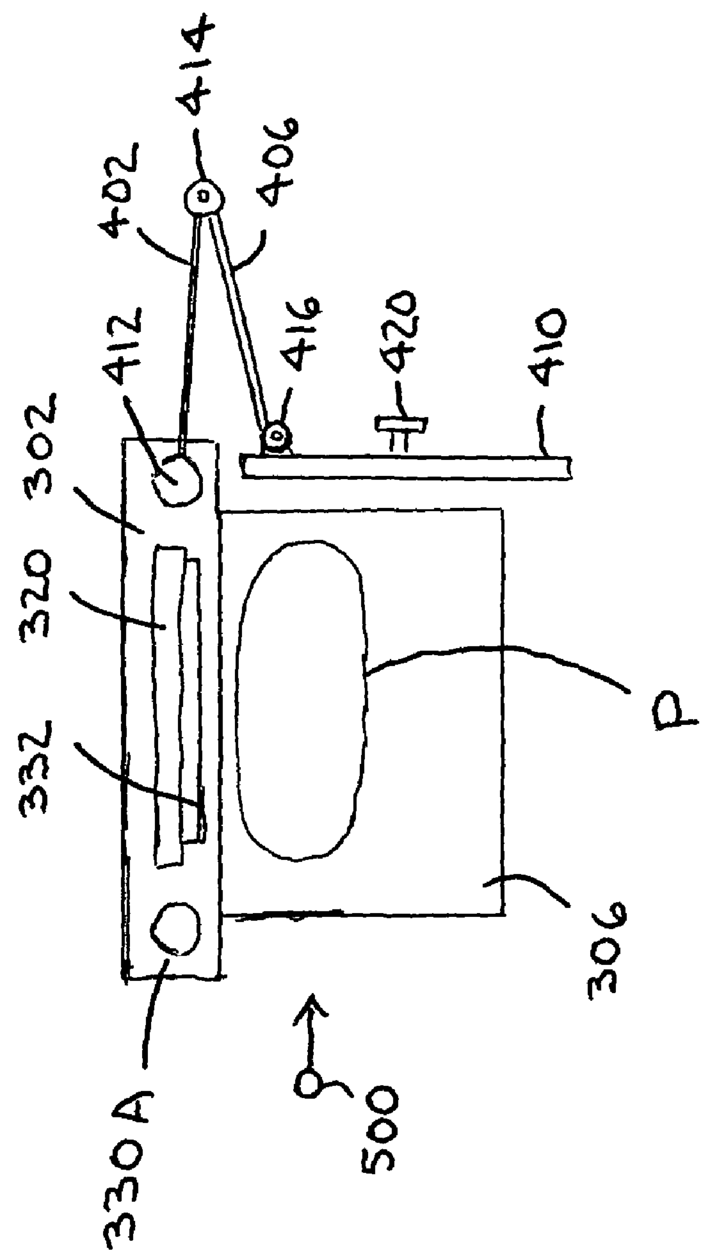
FIG. 2 shows details of the device of FIG. 1.

FIG. 2 shows a view looking down on just the seat area 300 of the fixture 100. The Bike 10 and Base 200 have been removed from this view for clarity. In this view the cassette mounting tray 410 has been pivoted to face a source of X-ray 500. The patient's torso P shown in cross section, is being x-rayed. This would give the left anterior view of the patient. The adjustable cassette holder 400 includes a rotatable rod 412 that can drop into a cylindrical hole 330A or 330B at either end of the mounting block 302. The arm section 402 is free to rotate nearly 360 degrees about either hole 330A, B with the seat back 320 and patient P being the only obstructions. The arm section 402 carries an elbow joint 414 about which the arm section 406 is free to rotate 360 degrees. The end of the arm section 406 carries another elbow joint 416 about which the cassette mounting tray 410 can rotate 360 degrees. The cassette mounting tray 410 can include an adjustment such as knob 420 to adjust for the size of x-ray cassette in place.

Figure 3:
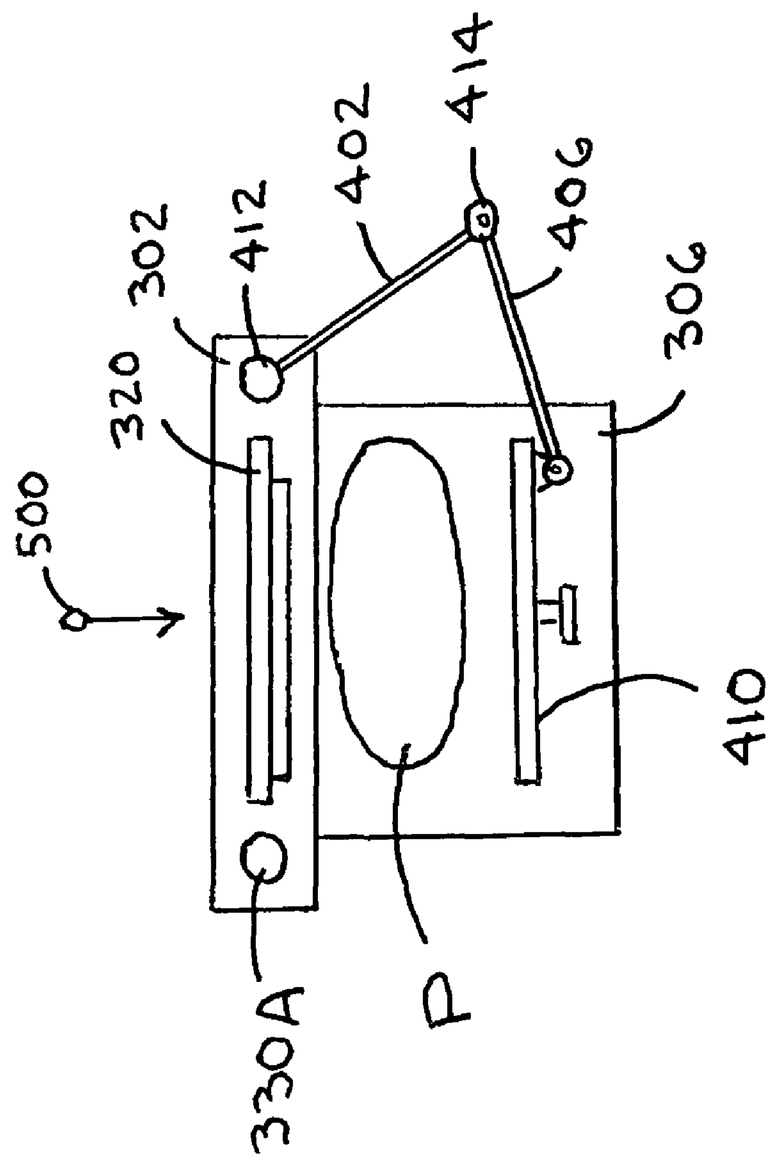
FIG. 3 shows details of the device.

FIG. 3 also shows a view of the fixture 100 looking down on the seat area 300 with the bike 10 and base 200 removed for clarity. In this view the cassette mounting tray 410 has been rotated to a second position in front of the patient's torso P, (Posterior-Anterior) again facing a source of X-rays 500. X-rays can penetrate the transparent acrylic seat back 320 and foam seat pad 332.

Figure 4:
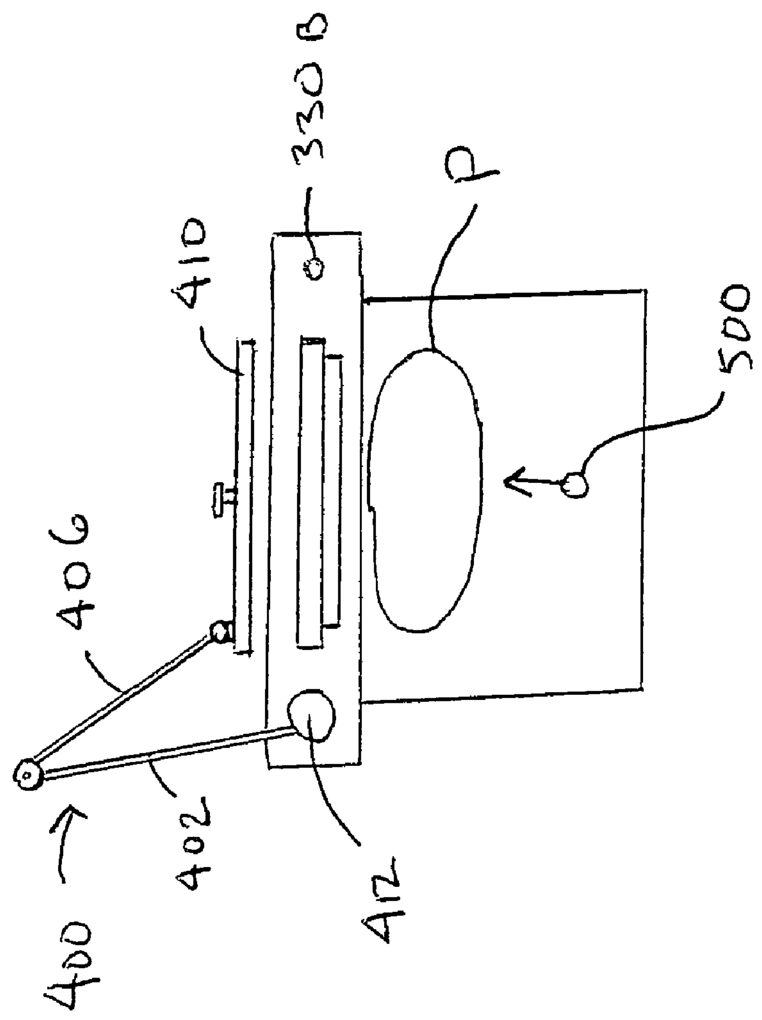
FIG. 4 shows details of the device.

FIG. 4 shows a view of the seat area 300 as shown in FIGS. 2 and 3 but with the adjustable cassette holder 400 and tray 410 in position to take a anterior-posterior view of the patient. FIG. 4 shows that the adjustable cassette holder 400 can be lifted out of mounting hole 330B and placed in hole 330A for images that require the cassette 410 to have access to the right side of the patient.

Figure 5:
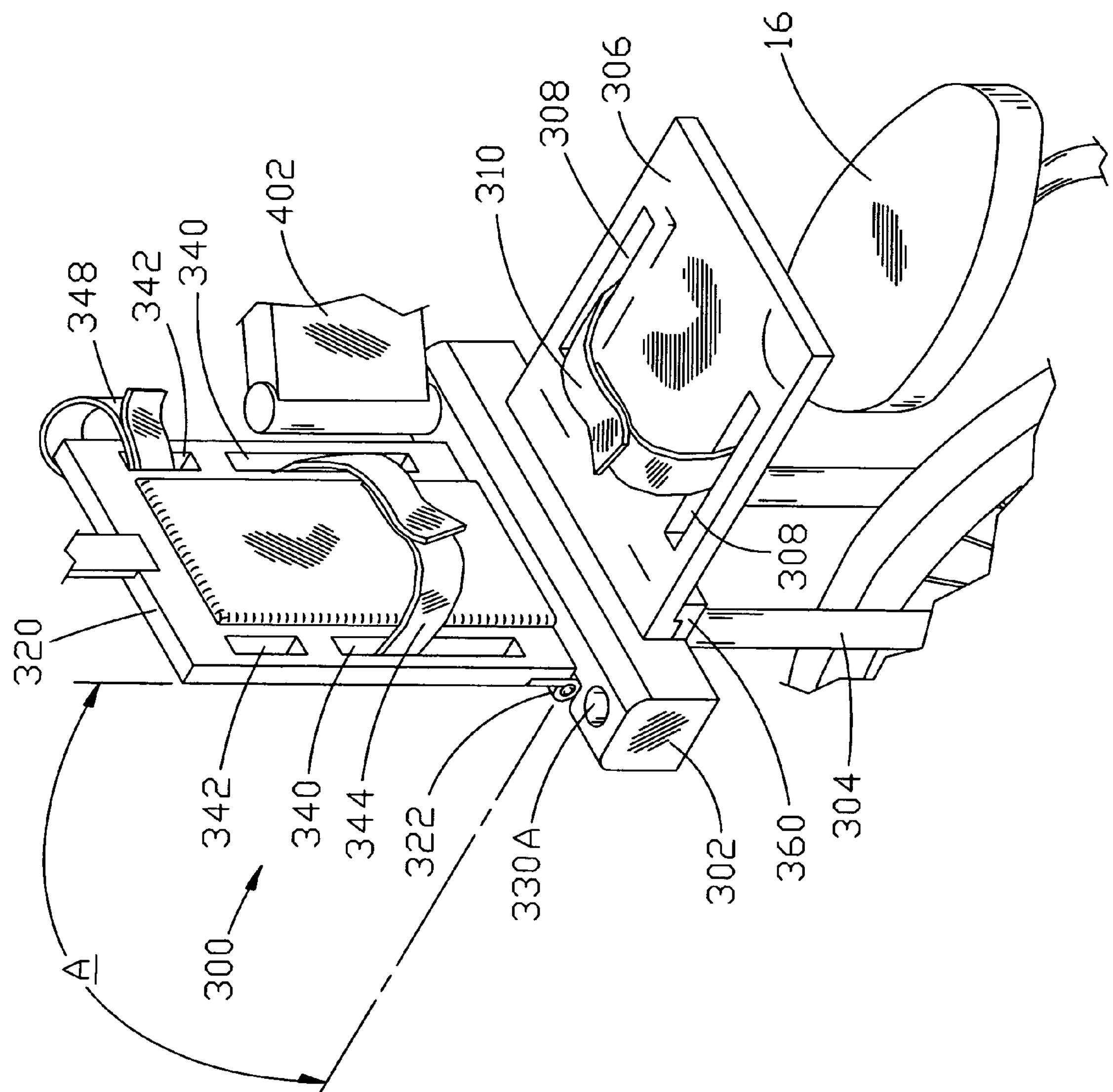
FIG. 5 shows details of the device.

FIG. 5 shows details of the seat area 300. The seat 300 can include a removable seat bottom 306 which can be a flat piece of acrylic material removably mounted to the mounting block 302. The seat bottom 306 can be located above the bike seat 16 such that when the seat bottom 306 is removed a patient could sit on the bike seat 16. There are slots 308 in the seat bottom 306 such that a restraining belt 310 can be used to secure a patient. The seat back 320 is attached to the mounting block 302 using upright supports 322. The seat back includes a foam pad 332 and slots 340 and 342. The slots 340 allow for one or several restraint belts 344 to support a patient. The higher slots allow for the use of small wrist restraints 348.

Figure 6:
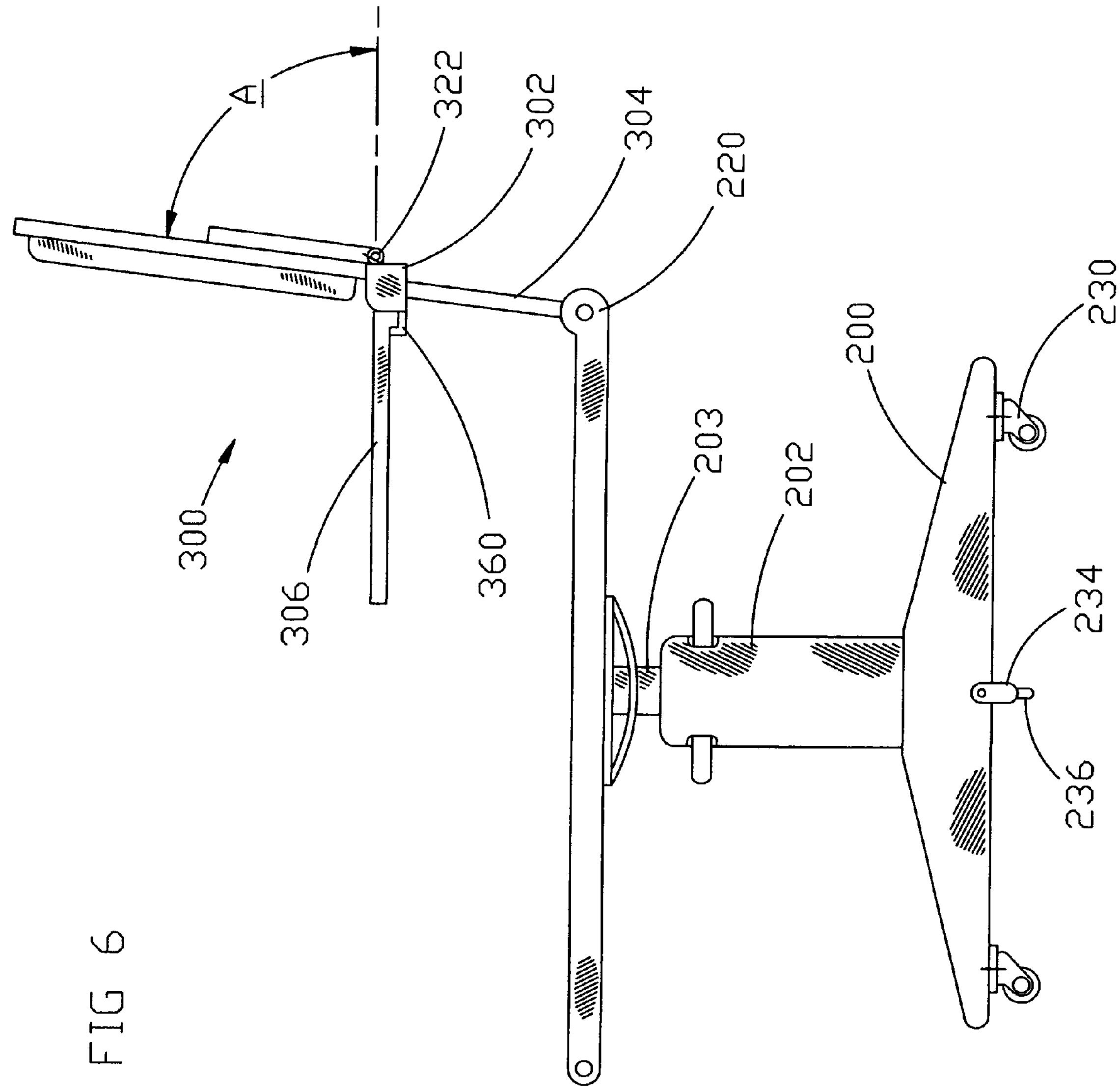
FIG. 6 shows a side view of the device.

FIG. 6 shows the x-ray fixture 100 with the bike 10 removed. The base 200 includes castors 230 that can be used to move the fixture 100 and can also be used in rough positioning of the fixture 100. The base 200 can then be locked in place using a foot operated latch 234, a plunger 236 can be released to engage the floor surface to hold the base 200 in place. The base 200 includes a plate 240 that is rotatably mounted to the piston 202, the plate 240 is attached to the two mounting arms 220 by welding or bolting for example. The seat 300 can include a hinge 322 that will allow the seat back 320 to rotate about 90 degrees as indicated by arrow A to lay horizontal or flat such that the back and seat. In some cases an x-ray technician will need to take images with the patient laying flat. The seat bottom 306 can include a angle bracket 360 on a back edge that allows the seat bottom to sit in a slot on the mounting block 302 such that the seat bottom 306 can easily be removed simply by lifting the seat bottom 306.

Figure 7:
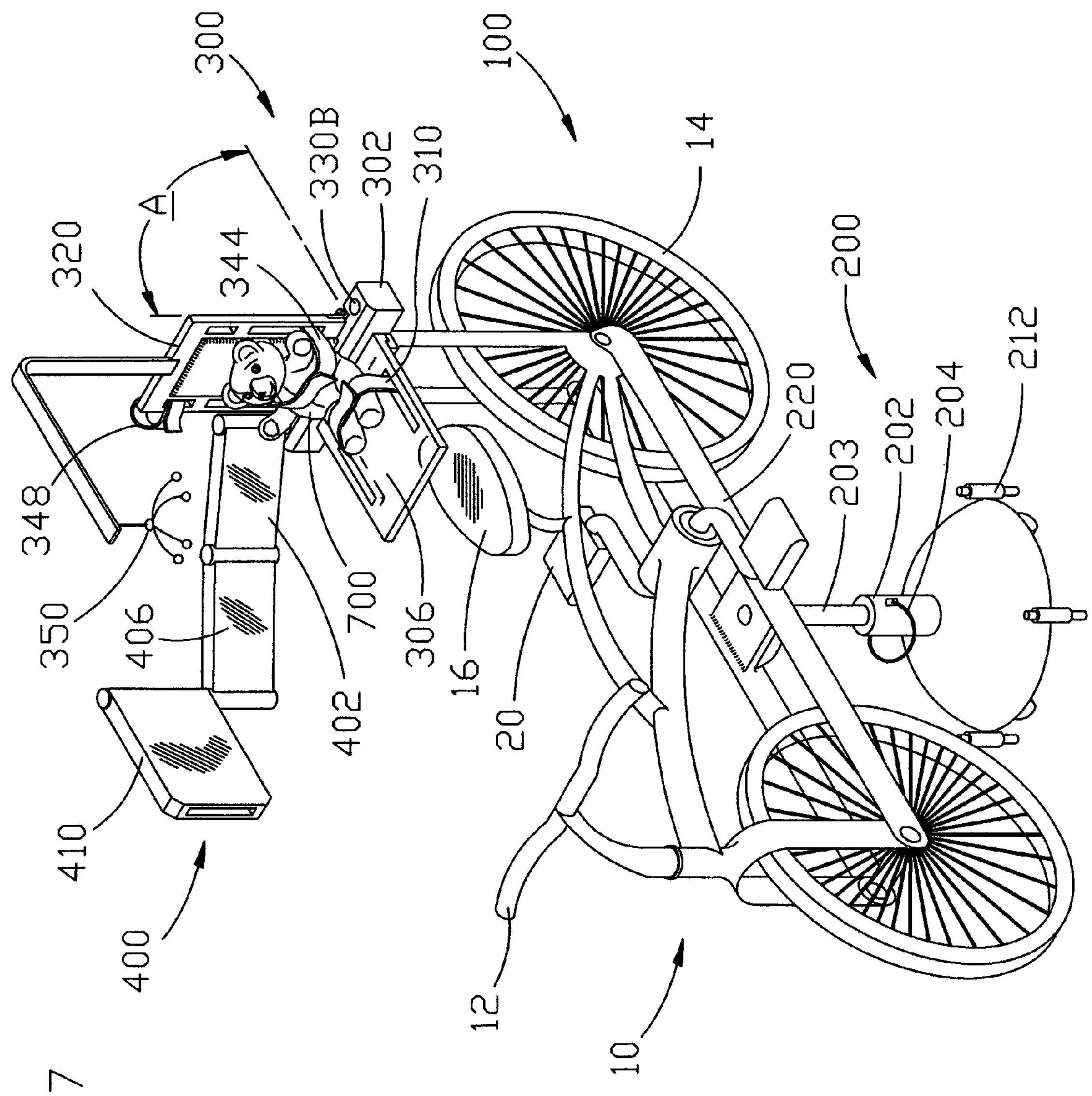
FIG. 7 shows the device in use.

FIG. 7 shows the fixture 100 ready for use. A toy such as a stuffed animal 700 is shown sitting on the seat 300 and has an arm restrained In use a stuffed animal such that might be a recognizable character can be placed in the seat 300 and held in place using restraints 344 or 310 such that when a child patient is brought into a room with the fixture 100 the first thing the child will see is a stuffed animal sitting on the bike 10. The child's attention will be drawn to the bike 10, the stuffed animal and the musical mobile 350. Experience shows that many children immediately ask to sit on the bike 10. The stuffed animal can be removed from the bike 10 and the child can be placed either on seat bottom 306 or on the bike seat 16 depending upon the age, maturity and size of the child and preference of the x-ray technician. Once on the seat 306, one or several restraints can be used to help a child hold still and to position the child as required for the X-ray image to be taken. The lap belt 310 can help hold the legs while a waist belt 344 can retrain the torso, wrist restraints 348 can be used to hold the arms up out of the x-ray image. Alternatively, a parent, for the personal touch, might hold a child's arms up out of the image. Once secure in the seat 300 the base 200 can be used to adjust the height of the patient to match the height of a source of x-ray 500.

Once the patient is positioned the x-ray cassette 410 can be rotated into position for any image required. Alternatively, the fixture 100 can be used with existing wall mounted x-ray cassettes, this is done simply by positioning the fixture 100 in front of the wall. The bike 10 and seat 300 can be rotated on the base 200 so that the 4 typical torso x-ray images right lateral, left lateral, posterior and anterior can be taken. If the cassette 410 is to be used, the technician simply grasps the cassette 410 and moves it to the position desired as shown in FIGS. 2, 3 and 4. The arms 402 and 406 will pivot to accommodate the movement of the cassette 410 and will hold the cassette 410 in place once it is positioned.

I claim:

1. A fixture for use in taking X-ray images of children comprising:

a height adjustable base;

a bike including a first seat portion;

at least one mounting arm, said at least one mounting arm including a first end connected to a front wheel of said bike and a second end connected to a rear wheel of said bike;

a second seat portion supported by said at least one mounting arm, said second seat portion including a back portion that is transparent to X-rays.

2. The fixture of claim 1 wherein said second seat portion includes a removable bottom portion mounted above said first seat portion such that a child can either sit on said second seat portion or on said first seat portion if said second seat portion is removed.

3. The fixture of claim 1 wherein said second seat portion includes a rotatable arm holding an X-ray cassette holder wherein said rotatable arm can be moved to positions allowing posterior, anterior, left lateral and right lateral X-rays of a child's torso to be taken.

4. The fixture of claim 1 wherein said back portion includes slots that allow for patient restraints to be attached to said back portion and said back portion includes a stuffed animal attachable to said back portion using said restraints.

5. A fixture for use in taking X-ray images of children comprising:

a height adjustable base;

a toy supported on said base, said toy including a first seat portion;

a second seat portion, said second seat portion being transparent to X-rays wherein said second seat portion includes a removable bottom mounted above said first seat portion such that a child can either sit on said second seat portion or on said first seat portion if said second seat portion is removed.

6. The fixture of claim 5 wherein said toy is a child's bike.

7. The fixture of claim 5 wherein said second seat portion includes a rotatable arm holding an X-ray cassette holder wherein said rotatable arm can be moved to positions allowing posterior, anterior, left lateral and right lateral X-rays of a child's torso to be taken.

8. The fixture of claim 7 wherein said fixture includes a seat back having slots that allow for patient restraints to be attached and said seat back includes a second toy attachable to said seat back using said restraints.

9. A fixture for use in taking X-ray images of children comprising:

a height adjustable base;

a toy mounted on said base;

a first seat portion supported by said base, said first seat portion including a portion that is transparent to X-rays;

a swivel arm carrying an x-ray cassette holder wherein said cassette holder can be movable from a first position in front of said first seat portion and to a second position behind said first seat portion and wherein said toy includes a second seat portion adjacent the first seat portion.

10. The fixture of claim 9 wherein said first seat portion includes a removable bottom mounted above said second seat portion such that a child can either sit on said first seat portion or on said second seat portion if said first seat portion is removed.

11. The fixture of claim 10 wherein said toy is a child's bike.

12. The fixture of claim 10 wherein said first seat portion includes said swivel arm holding said x-ray cassette holder wherein said swivel arm can be moved to positions allowing posterior, anterior, left lateral and right lateral X-ray images of a child's torso to be taken.

13. The fixture of claim 10 wherein said first seat portion includes a seat back having patient restraints and said seat back includes a stuffed animal attachable to said seat back using said restraints.

* * * * *